US012605097B2

(12) United States Patent
Palanisamy et al.

(10) Patent No.: US 12,605,097 B2
(45) Date of Patent: Apr. 21, 2026

(54) METHOD AND SYSTEM FOR SENSOR SIGNALS DEPENDENT DIALOG GENERATION DURING A MEDICAL IMAGING PROCESS

(71) Applicant: KONINKLIJKE PHILIPS N.V., Eindhoven (NL)

(72) Inventors: Krishnamoorthy Palanisamy, Bangalore (IN); Rithesh Sreenivasan, Bengaluru (IN); Rajendra Singh Sisodia, Bhopal (IN); Sarif Kumar Naik, Bangalore (IN); Gereon Vogtmeier, Aachen (DE); Mark Thomas Johnson, Arendonk (BE); Steffen Weiss, Hamburg (DE); Nagaraju Bussa, Bangalore (IN); Christopher Günther Leussler, Hamburg (DE)

(73) Assignee: Koninklijke Philips N.V., Eindhoven (NL)

( * ) Notice: Subject to any disclaimer, the term of this patent is extended or adjusted under 35 U.S.C. 154(b) by 377 days.

(21) Appl. No.: 18/036,181

(22) PCT Filed: Nov. 10, 2021

(86) PCT No.: PCT/EP2021/081171
§ 371 (c)(1),
(2) Date: May 10, 2023

(87) PCT Pub. No.: WO2022/101232
PCT Pub. Date: May 19, 2022

(65) Prior Publication Data
US 2024/0008783 A1      Jan. 11, 2024

(30) Foreign Application Priority Data

Nov. 12, 2020    (EP) ..................................... 20207197

(51) Int. Cl.
*A61B 5/16* (2006.01)
*A61B 5/00* (2006.01)
(Continued)

(52) U.S. Cl.
CPC ............ *A61B 5/165* (2013.01); *A61B 5/4803* (2013.01); *G06V 40/174* (2022.01); *G10L 25/63* (2013.01); *G16H 10/20* (2018.01)

(58) Field of Classification Search
None
See application file for complete search history.

(56) References Cited

U.S. PATENT DOCUMENTS

2012/0290324 A1* 11/2012 Ribbing ................. G16H 70/20
                                                                    705/3
2020/0205748 A1*  7/2020 Pautsch .................. A61B 6/032
(Continued)

FOREIGN PATENT DOCUMENTS

EP          1072994 B1      1/2001
EP          3473181 A1      4/2019
(Continued)

*Primary Examiner* — Dov Popovici

(57)                    ABSTRACT

A system (100) for sensor signals dependent dialog generation during a medical imaging process is described. The system includes a processor, and a computer readable medium that stores a computer program element, which when executed by the processor, causes the processor to: measure condition data of a patient; analyze the condition data of the patient to determine biometric and physical condition data of the patient; and generate questionnaires data for obtaining real-time feedback from the patient during the medical imaging process. The questionnaires data is based on a parameter of the medical imaging process and on the determined biometric and physical condition data of the patient.

20 Claims, 4 Drawing Sheets

(51) Int. Cl.
    *G06V 40/16*        (2022.01)
    *G10L 25/63*        (2013.01)
    *G16H 10/20*       (2018.01)

(56)            References Cited

U.S. PATENT DOCUMENTS

2022/0414877 A1 * 12/2022 Krafft .................. G06T 7/0012
2024/0221950 A1 * 7/2024 Kollada ............... A61B 5/0205

FOREIGN PATENT DOCUMENTS

| WO | 2012052880 A2 | 4/2012 |
| WO | 2015134953 A2 | 9/2015 |
| WO | 2019081915 A1 | 5/2019 |
| WO | 2019220428 A1 | 11/2019 |

* cited by examiner

METHOD AND SYSTEM FOR SENSOR SIGNALS DEPENDENT DIALOG GENERATION DURING A MEDICAL IMAGING PROCESS

CROSS REFERENCE TO RELATED APPLICATIONS

This application is a U.S. national phase application of International Application No. PCT/EP2021/081171 filed on Nov. 10, 2021, which claims the benefit of EP application Ser. No. 20/207,197.3 filed on Nov. 12, 2020 and is incorporated herein by reference.

FIELD OF THE INVENTION

The invention relates to a system and method for sensor signals dependent dialog manager for capturing patient's state and relevant action generation. In particular, the present invention relates to a system and a method and a system for sensor signals dependent dialog generation during a medical imaging process, to a method of training a machine-learning model, to a computer program element, and to a computer readable medium.

BACKGROUND OF THE INVENTION

EP 3 473 181 A1 describes methods for operating a medical image recording device, image recording device, computer program and electronically readable data carrier. The therein described device comprises a speech interaction system with at least a noise of the patient receiving microphone and at least one speaker to the patient, wherein— sounds originating from the patient are recorded by means of the microphone and evaluated by a speech recognition unit of the speech interaction system for determining patient information describing the condition of the patient and/or the content of spoken words.

During autonomous imaging, there are several situations when the patient might be alone in the preparation phase, the scanning phase but also after the scan. During the Magnetic resonance imaging, MRI, or computed tomography, CT, procedure, the patient is isolated in the modality room and is provided with some instructions to comply with.

These instructions could be about being still, holding of breath at intervals and not moving for a certain amount of time. The patient is given a rough idea of the time needed for the scan. The patient also has no sense of time progress when undergoing the procedure.

In some scenarios, the patient may feel anxiety and discomfort during the scan or the medical imaging process. This may be due to the longer duration of the scan than the expected, changes in other biometric conditions, or similar and corresponding aspects.

However, in autonomous imaging scenarios, the patient may not be able to express clearly their feedback or their anxiety during the scan or during the medical imaging process.

SUMMARY OF THE INVENTION

There may therefore be a need for improved medical imaging systems. The object of the present invention is achieved by the subject matter of the independent claims where further embodiments are incorporated in the dependent claims. It should be noted that the following described aspect of the invention equally applies to the system and the method, to a method of training a machine-learning model, to a computer program element, and to a computer readable medium.

According to a first aspect of the invention there is provided a system for sensor signals dependent dialog generation during a medical imaging process, the system comprising a sensor module, configured to measure condition data of a patient; a processor module, configured to analyze the condition data of the patient to determine biometric and physical condition data of the patient; a dialog data generation module, configured to generate questionnaires data for obtaining real-time feedback from the patient during the medical imaging process, wherein the questionnaires data is based on a parameter of the medical imaging process and on the determined biometric and physical condition data of the patient.

The present invention in contrast to the prior art allows automating the method for obtaining real-time feedback from the patient during the medical imaging process or during a single scan of the medical imaging process.

The present invention advantageously uses automated generation of the relevant questionnaires based on patient psychological and physical conditions to get the desired feedback.

The present invention advantageously uses automated system to continuously monitor the patient's biometric, physiological or physical condition to obtain the relevant feedback to take appropriate subsequent actions.

The present invention allows to qualify if the patient has understood the questions from the facial and physical expressions exhibited by the patient. The present invention advantageously uses sensory input and/or feedback data to make the patient more comfortable by making the patient flexible to provide the feedback using simple gestures, speech commands, and facial expressions including lip reading.

The present invention advantageously allows an improved workflow due to better patient cooperation and reducing patient anxiety.

According to an exemplary embodiment of the present invention, the sensor module is further configured to measure audio data of a patient and wherein the processor module is further configured to analyze the measured audio data of the patient to perform emotion recognition and to determine a comfort level of the patient.

According to an exemplary embodiment of the present invention, the comfort level of the patient may for instance refer to a level describing physical pain, acoustic noise, a visual stimuli or immobilization or movement restrictions or a sleep disturbance affecting the patient.

According to an exemplary embodiment of the present invention, the sensor module is further configured to measure video data of a patient and wherein the processor module is further configured to analyze the measured video data of the patient to perform emotion recognition and to determine a comfort level of the patient.

According to an exemplary embodiment of the present invention, the emotion recognition comprises at least one of facial recognition, voice recognition, and gesture recognition.

According to an exemplary embodiment of the present invention, the sensor module is further configured to measure feedback data of a patient and wherein the processor module is further configured to analyze the measured feedback of the patient to control the medical imaging process.

According to an exemplary embodiment of the present invention, the parameter of the medical imaging process comprises at least one of the following: a scan type of the medical imaging process, scan sequence of the medical imaging process, a time period of a scan of the medical imaging process, a targeted part of the patent of the of the medical imaging process.

According to an exemplary embodiment of the present invention, the dialog data generation module is configured to generate questionnaires data to minimize an amount of feedback data required from the patient.

According to an exemplary embodiment of the present invention, the processor module comprises a neural network is and the neural network is configured to optimize the generating of the questionnaires data based on the parameter of the medical imaging process and the determined biometric and physical condition data of the patient.

In another aspect still, there is provided a computer program element, which, when being executed by at least one processing unit, is adapted to cause a method to perform the method according to the previous aspect.

In another aspect still, there is provided at least one computer readable medium having stored thereon the program element, or having stored thereon the machine learning module.

In general, the "machine learning" may include a programmed classification based on algorithm that build a model based on sample data, known as "training data", in order to make predictions or decisions without being explicitly programmed to do so.

Some machine learning algorithms are model-based. A model based ML algorithm operates to adjust parameters of a machine learning model. This adjustment procedure is called "training".

The model is thus configured by the training to perform the task. ML algorithms also include instance-based learning. Task performance by the ML algorithm improves measurably, the more new training data is used in the training. The performance may be measured by objective tests when feeding the system with test data. The performance may be defined in terms of a certain error rate to be achieved for the given test data.

BRIEF DESCRIPTION OF THE DRAWINGS

Exemplary embodiments of the invention will now be described with reference to the following drawings, which, unless stated otherwise, are not to scale, wherein.

DETAILED DESCRIPTION OF EMBODIMENTS

Figure 1:
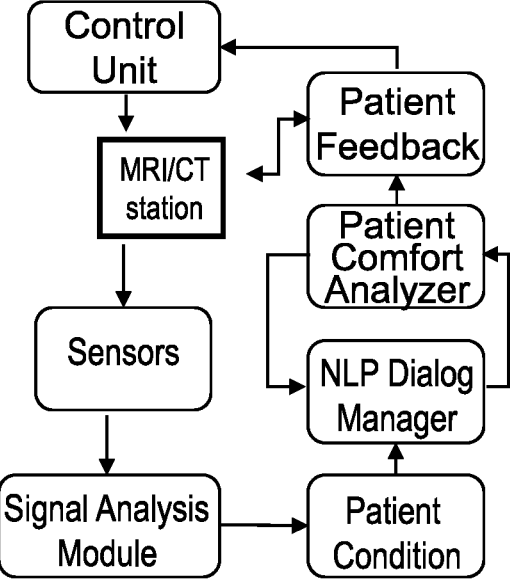
FIG. 1 shows a flowchart diagram of functional modules according to an exemplary embodiment of the present invention.

FIG. 1 shows a flowchart diagram of functional modules. According to an exemplary embodiment of the present invention, the block diagram shown in FIG. 1 illustrates how all the different modules described earlier are connected in realizing the proposed system.

According to an exemplary embodiment of the present invention, the process may start with continuously monitoring the various sensors data that include:

i) Sensors that monitor patient psychological conditions (ECG, EMG, Temperature, BP, and SPO2, or corresponding parameters or conditions)

ii) Cameras for face recognition & patient motion detection (can also be used for heart rate and breathing detection)

iii) Microphone for speech and voice emotion recognition iv) Integrated pain sensor in mattress based on electromagnetic sensor v) Skin conductance sensors such as GSR vi) The output of each sensor module is analyzed by an AI module to determine the patient's psychological and physical condition.

vii) The patient psychological/biometric condition is continuously estimating the variations in the patient's vital parameters (like oxygen saturation, heart rate, blood pressure).

viii) The stress level is realized by analyzing the facial expressions, using the sequence of images obtained from one or multiple cameras using the pre-trained AI models.

According to an exemplary embodiment of the present invention, the stress level identification module may also use the output of the biometric AI model as one of the input features. Initially, a supervised AI model is realized using the known ground truth samples that can be obtained by feedback from the patient as labels.

According to an exemplary embodiment of the present invention, the algorithm may be a combination of a machine learning approach for the estimation of the current stress level (like SVM, CNN, etc.,), and a machine learning approach for predicting the development of the stress level during the next few minutes (such as RNN or LSTM).

According to an exemplary embodiment of the present invention, the stress level is assessed by focusing on the output of two specific vital parameter sensors i) the GSR sensor, where the stress level is registered as the sum of the peak intensities (more accurately the sum of the rising edges of the peaks above background level) taken as a running average over a period of time of a few minutes and/or ii) the periodicity of the heart rate variation of the patient, whereby a stronger periodicity is associated with a more relaxed patient.

According to an exemplary embodiment of the present invention, optionally for ii) if the heart rate variation is both periodic and furthermore synchronous with the breathing rate (measured by a third vital parameter sensor) of the patient, then the patient may be considered to be even more relaxed.

According to an exemplary embodiment of the present invention, the pain level of the patient may be obtained from an integrated pain sensor in mattress or attached to any convenient peripheral point of the patient where many sweat glands are present, for instance such as two adjacent fingers on one hand, two electrodes on the inside of a wristband, attached to the foot or the like based on the electromagnetic sensor or from skin, such as GSR, galvanic skin response.

According to an exemplary embodiment of the present invention, the patient motion level or motion grade, for instance it is discriminated between no, minimal, medium, severe motion level, is estimated by analyzing the sequence of images obtained from the camera or the output of the motion sensors or the combination of them both According to an exemplary embodiment of the present invention, the patient comfort level is estimated detecting the emotion level of the patient using facial expression, other physical movements and the vital parameter measurements indicated above.

According to an exemplary embodiment of the present invention, specifically, in a stressful situation such as undergoing an autonomous scan, the emotional level is often associated with the total amount of stress encountered—the valence of the emotion becomes more negative as the total amount of stress builds up.

According to an exemplary embodiment of the present invention, this is further assessed by for example measuring the integral sum during the entire measurement period of the peak intensities in the GSR measurement (as opposed to the running average described above)

Figure 2:
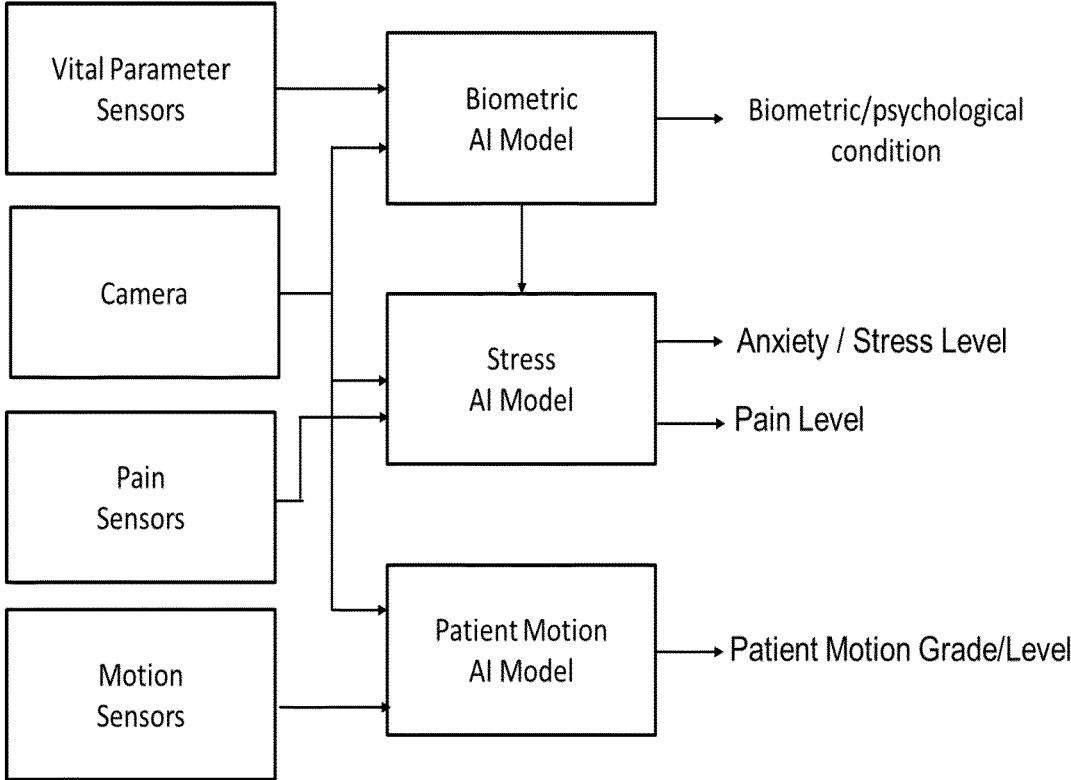
FIG. 2 shows data representing patient psychological and physical condition estimation according to an exemplary embodiment of the present invention.
Figure 3:
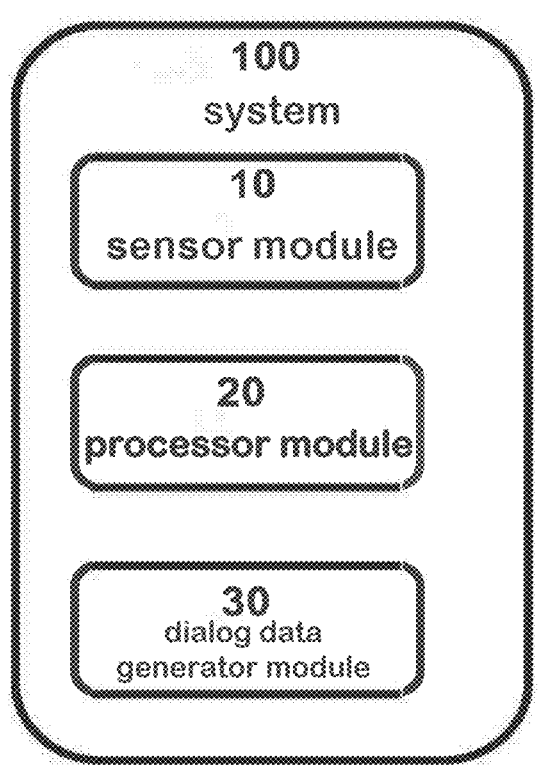
FIG. 3 shows a block diagram of a computer implemented system for sensor signals dependent dialog generation during a medical imaging process according to an exemplary embodiment of the present invention.
Figure 4:
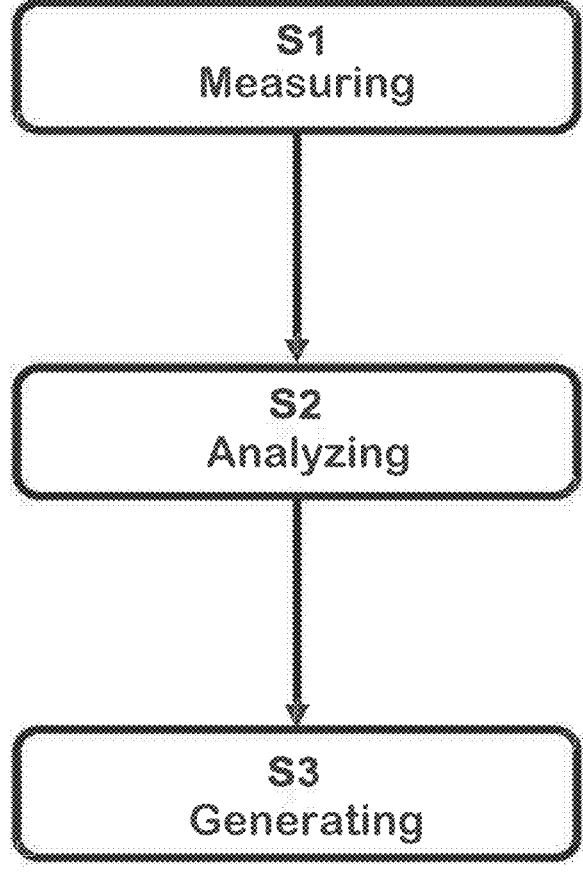
FIG. 4 shows a flow chart of a method for sensor signals dependent dialog generation during a medical imaging process according to an exemplary embodiment of the present invention.

The block diagram shown in FIG. 2 illustrates how the output of the different sensor can be used in determining the patient psychological and physical condition According to an exemplary embodiment of the present invention, in the next step, the output of these AI models are used to generate the relevant questionnaires to get the required feedback more easily and comfortably.

According to an exemplary embodiment of the present invention, the questions may be predefined and rated by simplicity and by answer range (closed questions (only "yes" and "no" as answers), half open questions ("colder", "warmer, "good", "bad", "better"), and open questions).

According to an exemplary embodiment of the present invention, the output of the patient condition module is used to select questions from these groups, so that questions are deliberately kept simpler in case of worse patient condition. During actual MR scans preferably only closed or half open questions are issued. This keeps answers short and so minimizes motion induced by answers. Secondly, lip reading can be applied to analyze the answers in the noisy environment because the answer range is small and mostly known.

According to an exemplary embodiment of the present invention, the list of questions can be generated as look-up table based on the sequence/stage of the scan per each of the anatomy scan. This list can be populated by analyzing the questions that are asked by the human technician in normal scans for a chosen patient profile.

According to an exemplary embodiment of the present invention, if the patient profile is related to OLD AGE, then the system needs to ask more questions in each of the phase of the scan. This list is populated by analyzing the population level data and generating contextual questions that depend on patient profile, stage of the scan and scan anatomy etc.

According to an exemplary embodiment of the present invention, the questionnaire data may include the instructions as well.

According to an exemplary embodiment of the present invention, the questions of the generated questionnaire data may include, without being limited to:

Are you feeling pain?
Are you feeling anxiety/discomfort?
Do you want to stop the scan for some time?
Do you want to stop the scan permanently?
Would you like to move your body a little bit to relax?
Would you like to know the remaining time for the scan?
Are you having difficulty in breathing?
Is it very cold?
Would you like to go to the rest room?

Are you feeling warm?

According to an exemplary embodiment of the present invention, the generated questionnaires are conveyed to patient either by visual text audio, haptic, bone conduction etc.

According to an exemplary embodiment of the present invention, in most scenarios, the patient may not be able to express clearly their feedback or their anxiety during the scan or the medical imaging process. Hence based on the more relevant questions, the patient under the examination can provide the feedback/respond by the simple form of gestures like movement hand or eye movement or simple voice commands like "yes" or "no" using the microphone.

According to an exemplary embodiment of the present invention, the vital parameter sensor may also be used to assess the response of the patient—as is known from lie detector technology.

According to an exemplary embodiment of the present invention, the relevant or more relevant questions can be generated based on the scan type, sequence of the scan, targeted anatomy, Patient physiological and psychological conditions.

According to an exemplary embodiment of the present invention, for instance, for a complete spine scan once the neck and upper back is over a question can be generated like "Do you want to relax/move your neck a little bit" as the patient would be trying to be still during the initial part of the scan and may need to relax a little bit. If the patient psychological condition is shown as "stress", the dialog generator will generate question related to stress, e.g. are you under stress? And if the question is affirmative, can also do the action generation, such as action to reduce stress by playing music etc.

Similarly, if the physiological condition of a patient is identified, e.g. increased HR/RR, question about his anxiety can be generated and upon confirmation, haptic solution can be deployed to reduce HR. In the instance of negative feedback is received than expected positive feedback, the scan procedure can be adapted or even stopped in the interest of the safety of the patient. This can be another action taken by the machine.

In another instance the patient panic reactions, going to sleep can be analyzed with an additional method using the combination images received from the camera and other sensors. For example, in breath-controlled scan, the system has to wake up the patient if patients go sleep and make sure they start to follow instructions. Another instance would be after administering the contrast to check if the patient is feeling comfortable.

According to an exemplary embodiment of the present invention, the CT contrast can induce a sense of heat flushing through the body. According to an exemplary embodiment of the present invention, a question can be "Are you feeling hot/warm" and based on the answer the patient can be reassured that this is normal.

According to an exemplary embodiment of the present invention, the NLP module can be implemented as a neural network classification model which is trained with a set of scan sequences, patient condition, time instance in the scan, targeted anatomy along with ground truth question/questionnaire. The trained model can then retrieve a question/questionnaire based on the inputs.

According to an exemplary embodiment of the present invention, the during a scan or oncology therapy session it should be avoided that the patients falls asleep or does loses consciousness during a sequence of different scans using a drowsiness detection. Often the patient falls asleep for a short time and shows up panic reaction when he wakes up. Additionally, communication between operator and patient is not possible.

According to an exemplary embodiment of the present invention, to prevent falling asleep actuators or nudging in combination with audio signals are used.

According to an exemplary embodiment of the present invention, the detection is realized using 3D sensing, for example radar or lidar, light detection and ranging, in combination with NLP response time of patient.

According to an exemplary embodiment of the present invention, the case of falling asleep a special communication protocol is applied: Hallo do not sleep, stay wake and additionally entertainment is modified and adapted to prevent falling asleep.

According to an exemplary embodiment of the present invention, when a series of different scans is started, each scan does have a short autonomous audio tag to inform or communicate the patient about the type of scan, which helps to reduce anxiety. The decision of the application of the audio tag is controlled by the AI algorithm, which directly classifies the emotional status of the patient. The tag informs the patient about the timing, robustness against motion etc. The tag can also be applied for scans in combination with therapy.

According to an exemplary embodiment of the present invention, microphone based communication during the MRI scan is in 90% of the regular scans not feasible. Technically the microphone signal including noise level cancellation may be supported by contactless reading of gesture and lips using 3D radar or lidar based approach. All signals from the different sensors are fed to an AI based SW for NLP.

According to an exemplary embodiment of the present invention, the communication is performed in environment/scans with strong noise level: For simple communication to allow the patient answering yes or no, or even more, it is propose to use a breathing response detector. The detector has a threshold and is activated, when the patient makes a short breath. A different sensing technology can be applied for the patient using sound bite communication. A wireless bite sensor is located in the mouth and allows to send signals to the communication interface.

According to an exemplary embodiment of the present invention, another instance allows also for analysis of the "trust level" that the patient develops using the interactive dialog manager. If the patient feels that the dialog manager is reacting in an appropriate way to the patient's concerns, questions and requests then via the sensors the relaxing mood and the acceptance would be analyzed and via such confirmation the system can continue as proposed by the algorithm.

In case the patient's reaction shows low trust levels and even higher anxiety level of the patient then either an alternative predefined approach could be selected as first escalation level and if that does not work also staff can be involved to improve the situation.

According to an exemplary embodiment of the present invention, the AI "learning" from managing several of these situations helps to optimize the system and build up a patient profile based best proposal strategy for the most successful dialog handling. At the same time the continuous control of the acceptance and "trust level" guarantees a safe environment for the patient using an autonomous system.

Another way of doing this is to give a confidence to the output of the reaction analyzer module. If the confidence is below certain threshold that means the feedback from the user is not well analyzed or detected. In this scenario, the system generates second level procedure, which helps in automatically connecting to remote staff for further steps and executions of the system.

According to an exemplary embodiment of the present invention, in the case of autonomous imaging workflow, these feedbacks are automatically processed by processing the images received from the camera (hand/eye gestures, lip reading) or using the speech to text recognition module when the feedback is conveyed in the form of speech commands.

According to an exemplary embodiment of the present invention, based on the feedback the control center of the scanner unit is informed to take the appropriate action.

One or more features described herein can be configured or implemented as or with circuitry encoded within a computer-readable medium, and/or combinations thereof. Circuitry may include discrete and/or integrated circuitry, a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user.

A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope of protection of the claims.

LIST OF REFERENCE SIGNS 10 sensor module
20 processor module
30 dialog data generator module
100 system
S1 Measuring
S2 Analyzing
S3 Generating

The invention claimed is:

1. A system for sensor signals dependent dialog generation during a medical imaging process, the system comprising:
a processor;
memory that stores a computer program, which when executed by the processor, causes the processor to:
measure condition data of a patient;
analyze the condition data of the patient to determine biometric and physical condition data of the patient; and
generate questionnaires data for obtaining real-time feedback from the patient during the medical imaging process, wherein the questionnaires data is based on a parameter of the medical imaging process and on the determined biometric and physical condition data of the patient.

2. The system of claim 1, wherein the computer program further causes the processor to: measure audio data of a patient, and analyze the measured audio data of the patient to perform emotion recognition and to determine a comfort level of the patient.

3. The system of claim 1, wherein the computer program further causes the processor to: measure video data of a patient; and analyze the measured video data of the patient to perform emotion recognition and to determine a comfort level of the patient.

4. The system of claim 2, wherein the emotion recognition comprises at least one of facial recognition, voice recognition, or gesture recognition.

5. The system of claim 1, wherein the computer program further causes the processor to obtain real-time feedback from the patient during the medical imaging process.

6. The system of claim 2, wherein computer program further causes the processor to: measure feedback data of a patient, and analyze the measured feedback of the patient to control the medical imaging process.

7. The system of claim 2, wherein the parameter of the medical imaging process comprises at least one of the following: a scan type of the medical imaging process, scan sequence of the medical imaging process, a time period of a scan of the medical imaging process, a targeted part of the patient of the of the medical imaging process.

8. The system of claim 2, wherein the computer program further causes the processor to generate questionnaires data to minimize an amount of feedback data required from the patient.

9. The system of claim 2, wherein the computer program further causes the processor to measure condition data of the patient in terms of a drowsiness detection for the patient and a dialog data generation module is configured to generate audio-or video-based wake-up signals for stimulating the patient based on the drowsiness detection.

10. The system of claim 2, wherein the computer program comprises a neural network, which is configured to optimize the generating of the questionnaires data.

11. A medical imaging device comprising the system of claim 2.

12. A method for sensor signals dependent dialog generation during a medical imaging process, the method comprising,
measuring condition data of a patient;
analyzing the condition data of the patient to determine biometric and physical condition data of the patient; and
generating questionnaires data for obtaining real-time feedback from the patient during the medical imaging process, wherein the questionnaires data is based on a parameter of the medical imaging process and on the determined biometric and physical condition data of the patient.

13. The method of claim 12, further comprising measuring audio data of a patient, and analyzing the measured audio data of the patient to perform emotion recognition and to determine a comfort level of the patient.

14. The method of claim 13, wherein the emotion recognition comprises at least one of facial recognition, voice recognition, or gesture recognition.

15. The method of claim 12, further comprising measuring video data of a patient and analyzing the measured video data of the patient to perform emotion recognition and to determine a comfort level of the patient.

16. The method of claim 12, further comprising obtaining real-time feedback from the patient during the medical imaging process.

17. The method of claim 12, further comprising measuring feedback data of a patient, and analyzing the measured feedback of the patient to control the medical imaging process.

18. The method of claim 12, wherein the parameter of the medical imaging process comprises at least one of the following: a scan type of the medical imaging process, scan sequence of the medical imaging process, a time period of a scan of the medical imaging process, a targeted part of the patient of the of the medical imaging process.

19. The method of claim 12, further comprising generating questionnaires data to minimize an amount of feedback data required from the patient.

20. The method of claim 12, further comprises measuring condition data of the patient in terms of a drowsiness detection for the patient and a dialog data generation module is configured to generate audio-or video-based wake-up signals for stimulating the patient based on the drowsiness detection.

\* \* \* \* \*